(12) United States Patent
Vuaridel et al.

(10) Patent No.: US 6,777,002 B1
(45) Date of Patent: Aug. 17, 2004

(54) PROCESS FOR MICROENCAPSULATION OF WATER SOLUBLE SUBSTANCES

(75) Inventors: Evelyne Vuaridel, Nyon (CH); Piero Orsolini, Martigny (CH)

(73) Assignee: Debio Recherche Pharmaceutique S.A., Martigny (CH)

( * ) Notice: Subject to any disclaimer, the term of this patent is extended or adjusted under 35 U.S.C. 154(b) by 0 days.

(21) Appl. No.: 09/958,806

(22) PCT Filed: Apr. 14, 2000

(86) PCT No.: PCT/CH00/00218

§ 371 (c)(1),
(2), (4) Date: Oct. 15, 2001

(87) PCT Pub. No.: WO00/62761

PCT Pub. Date: Oct. 26, 2000

(30) Foreign Application Priority Data

Apr. 15, 1999 (EP) ............................................. 99107570

(51) Int. Cl.$^7$ .............................. A61K 9/14; A61K 9/16
(52) U.S. Cl. ........................ 424/489; 424/490; 424/491
(58) Field of Search .................................. 424/489–491

(56) References Cited

U.S. PATENT DOCUMENTS

| | | | |
|---|---|---|---|
| 3,691,090 A | | 9/1972 | Kitajima et al. |
| 3,960,757 A | | 6/1976 | Morishita et al. |
| 5,238,714 A | | 8/1993 | Wallace et al. |
| 5,654,008 A | * | 8/1997 | Herbert et al. ............... 424/489 |
| 6,090,925 A | * | 7/2000 | Woiszwillo et al. ......... 530/410 |

FOREIGN PATENT DOCUMENTS

| | | |
|---|---|---|
| EP | 0 585 151 | 3/1994 |
| GB | 1 297 476 | 11/1972 |
| GB | 2 234 896 | 2/1991 |
| GB | 2 257 909 | 1/1993 |
| WO | 97/41837 | 11/1997 |

OTHER PUBLICATIONS

International Cosmetic INgredient Dictionary and Handbook, vol. 2, 7$^{th}$ edition, pp 1670–1672.*

* cited by examiner

Primary Examiner—Collamudi S. Kishore
Assistant Examiner—Isis Ghali
(74) Attorney, Agent, or Firm—Nixon & Vanderhye P.C.

(57) ABSTRACT

The present invention relates to a process for the preparation of microparticles, with an extremely high encapsulation rate, comprising a water-soluble substance in a biodegradable polymer, said water-soluble substance and said biodegradable polymer being first incorporated in an organic liquid phase comprising at least one organic non-water miscible solvent. The organic phase is poured into an aqueous liquid phase having a volume which is sufficient to dissolve said organic solvent, said aqueous phase containing a surfactant, the resulting organic-aqueous phase being homogenised in order to perform in one single step the microparticle formation and the organic solvent removal. The thus obtained microparticles show surprisingly good agent retention qualities.

9 Claims, No Drawings

PROCESS FOR MICROENCAPSULATION OF WATER SOLUBLE SUBSTANCES

The present invention relates to a process for the preparation of microparticles comprising a water-soluble substance in a biodegradable polymer.

Many different methods of preparation of microspheres are described in the literature (Herrmann et al., European Journal of Pharmaceutics and Biopharmaceutics 45 (1998) 75–82). The methods presently used for the preparation of microspheres from hydrophobic polymers are organic phase separation and solvent removal techniques.

The solvent removal techniques can be divided into solvent evaporation, solvent extraction, spray drying and supercritical fluid technology. In solvent evaporation or solvent extraction techniques, a drug containing organic polymer solution is emulsified into an aqueous or another organic solution. The drug is dissolved, dispersed or emulsified in the inner organic polymer solution.

These solvent removal techniques for production of microspheres by evaporation or extraction necessitate the step of preparing a stable emulsion of organic droplets before solvent removal. The size and characteristics of the final microspheres depend on this step during which a stable emulsion in the presence of the solvent is a prerequisite. The proportions of organic solvent and aqueous phase in the solvent removal methods are carefully maintained so as to control the solvent migration in the aqueous phase. Below a certain ratio organic solvent/aqueous phase, the formation of droplets is not possible any more (see H. Sah, "Microencapsulation techniques using ethyl acetate as a dispersed solvent: effects of its extraction rate on the characteristics of PLGA microspheres," Journal of controlled release, 47 (3) 1997, 233–245). In some methods, solvent is even added to the aqueous phase in order to saturate it and to prevent the solvent migration during the formation of the primary emulsion.

Several related patents and published applications describe various aspects of these processes.

EP 0 052 105 B2 (Syntex) describes a microcapsule prepared by the phase separation technique using a coacervation agent such as mineral oils and vegetable oils.

EP 0 145 240 B1 (Takeda) discloses a method for encapsulating a water soluble compound by thickening the inner phase of a W/O emulsion, building a W/O/W and subjecting the emulsion to an "in water drying" process. This method brings different drawbacks such as: the necessity of using a thickening agent to retain the drug, and the multi-step procedure including two emulsification steps and the "in water drying" step.

EP 0 190 833 B1 (Takeda) describes a method for encapsulating a water soluble drug in microcapsules by increasing the viscosity of a primary W/O emulsion to 150–5,000 cp (by the procedure of increasing the polymer concentration in the organic phase or by adjusting the temperatures) prior to formation of a second W/O/W emulsion which is then subjected to "in water drying". The drawbacks of this procedure are the complexity of the necessary steps, including formation of two emulsions (W/O and W/O/W) one after the other, and the step of "in-water drying".

U.S. Pat. No. 5,407,609 (Tice/SRI) describes a microencapsulation process for highly water soluble agents. This process involves the distinct steps of forming a primary O/W emulsion, the external aqueous phase being preferably saturated with polymer solvent. This O/W emulsion is then poured to a large volume of extraction medium in order to extract immediately the solvent. The drawback of this method is that the O/W emulsion is formed in the presence of the organic solvent in a small volume. The solvent is subsequently removed by extraction in a large aqueous volume. The polymeric droplets are prevented to harden in the primary emulsion, allowing the migration of the drug into the external phase.

WO 95/11008 (Genentech) describes a method for the encapsulation of adjuvants into microspheres. The process comprises the three distinct steps of preparing a primary W/O emulsion, followed by the production of a W/O/W and finally the hardening of the microspheres by extraction of the solvent. As already mentioned above, the drawback of such a method is the complication due to a multi-step procedure separating droplet production from solvent elimination.

EP 0 779 072 A1 (Takeda) describes an "in-water drying" method used for the removal of solvent after production of a W/O/W or a O/W emulsion. It is mentioned that the O/W method is preferable for active substances insoluble or sparingly soluble in water.

It is an object of the present invention to provide with a new process for the preparation of microparticles comprising water soluble biologically active substances.

It is still further an object of the present invention to provide with a new process for the preparation of microparticles of high encapsulating efficiency comprising water soluble biologically active substances.

It is further an object of the present invention to provide with a process which allows for a reduction of time of exposure of water soluble active substances to external water phase in the production of microparticles.

It is further an object of the present invention to avoid the formation of specific emulsions, and the problems they have caused as described in the prior art in the production of microparticles comprising water soluble active substances.

To these effects, the present invention relates to a process for the preparation of microparticles with an extremely high encapsulation rate thanks to the optimal reduction of diffusion for the substance to be encapsulated.

More precisely, the present invention relates to a process for the preparation of microparticles comprising at least one water-soluble substance in at least one biodegradable polymer, said water-soluble substance and said biodegradable polymer being first incorporated in an organic liquid phase comprising at least one organic non-water miscible solvent, said organic phase being then poured into an aqueous liquid phase having a volume which is sufficient to dissolve said organic solvent, said aqueous phase containing a surfactant, the resulting organic-aqueous phase being homogenised in order to perform in one single step the microparticle formation and the organic solvent removal.

The methods available up to now for encapsulating certain compounds and agents, and particularly, water soluble compounds and agents, were not efficient enough for encapsulating water soluble biologically active substances due to the high affinity that water soluble biologically active substances have with the aqueous phase.

The present invention has found a solution to this problem by reducing the time required for encapsulating water soluble biologically actives substances, and therefore avoiding the problem of formation of the primary emulsion and solvent removal steps which were far too long and allowed the migration of the water soluble biologically active substances into the external aqueous phase.

The microparticle formation and their hardening is performed in one single step. After homogenisation, the dispersion is directly filtered. The particles are then harvested and optionally lyophilised.

Using the process of the present invention offers the advantage of providing an encapsulation efficiency greater than 50% or 80%.

Furthermore, in the process of the present invention, it has been surprisingly found that it is possible to obtain microparticles with an extremely high encapsulation efficiency of water soluble active substances using a new one step O/W or W/O/W homogenisation process.

One of the specific features in the process of the present invention is characterised by the fact that no stable primary emulsion comprising organic solvent droplets occurs. Avoiding such a step results in a better retention of the water-soluble substance.

Furthermore, because of the almost instantaneous lack of organic solvent when the polymer precipitates and captures the water-soluble substance, no further emulsion stage is observed. The microparticles can thus be directly harvested after their formation.

Because the microparticle formation and the solvent removal are done together in one single step in this process, the water soluble biologically active substance is quickly kept inside the microparticles which have an impermeable wall. Thereby any diffusion external to the microparticles is at a low level, and the encapsulation rate is very high.

It must also be mentioned that the process of the present invention avoids the steps of solvent extraction and of solvent evaporation.

The organic solvents used in the process of the present invention are non-water miscible solvents such as esters (e.g. ethyl acetate, butyl acetate), halogenated hydrocarbons (e.g. dichloromethane, chloroform, carbon tetrachloride, chloroethane, dichloroethane, trichloroethane), ethers (e.g. ethyl ether, isopropyl ether), aromatic hydrocarbons (e.g. benzene, toluene, xylene), carbonates (e.g. diethyl carbonate), or the like. Although these solvents are generally classified by the person skilled in the art as non-water miscible solvent, they are actually sparingly miscible in water, having a low solubility in water. For instance, for ethyl acetate and dichloromethane, the solubility is resp. 8.70% and 1.32% (by weight) in water at 20–25° C. (see A. K. Doolittle Ed., Properties of individual solvents, in The technology of solvents and plasticizers, chpt. 12. Wiley, N.Y., 1954, pp. 492–742). One of the preferred solvent is ethyl acetate.

The above-mentioned organic solvents can be used alone or in mixtures of two or more different solvents.

The volume of the aqueous phase must be sufficient to dissolve, or extract, the total amount of organic solvent used. If this is not the case, the microparticles cannot be sufficiently hardened. Those "soft" microparticles may therefore melt among each others during the filtration process.

Accordingly, the amount of organic solvent is kept as low as possible to get a viscous organic phase and to minimise the necessary volume of the aqueous phase. In all of the following embodiments, the volume of the aqueous phase is chosen to be capable of dissolving at least the complete amount of organic solvent.

The maximal value of the ratio solvent/water (w/w) in the present invention should therefore preferably be 0.087 and 0.013 for ethyl acetate and dichloromethane respectively. In the examples given below, the ratio ethyl acetate/aqueous phase ranges from 0.007 to 0.06. The encapsulating efficiency improves if the volume of aqueous phase increases.

A surfactant is added to the aqueous phase in order to keep the precipitating biodegradable polymer in fine independent particles. An ideal surfactant gives a viscosity to the aqueous phase that approaches the viscosity of the organic phase.

An electrolyte may also be optionally added to the aqueous solution to create repulsion between the particles and preventing aggregation. As a preferred electrolyte, sodium chloride is used in the aqueous phase and leads to a higher encapsulating efficiency.

The aqueous solution can also be buffered to obtain good pH conditions for the drug concerning stability and release.

When a solvent such as ethyl acetate is used, it has been surprisingly found that the encapsulation efficiency is increased when using cold solutions, by optimising the solubility of the solvent in water, by reducing the aqueous solubility of the drug, and by slowing down its diffusion. In other words, the present invention achieves the effect of further reducing the already small amount of diffusion of internal particle substances to the exterior.

A water-soluble biologically active substance is dispersed as such or as an aqueous solution into one of the above-mentioned non-miscible organic solvent. In some embodiments of the process, the biologically active substance is present in solid state in the organic phase during the entrapment procedure, thus slowing down the solubilisation into the aqueous liquid phase.

The thus obtained liquid organic phase containing the biologically active substance is used to dissolve the biodegradable polymer.

The appropriate biodegradable polymers comprise poly (lactides), poly(glycolides), copolymers thereof or other biodegradable polymers such as other aliphatic polymers, polycitric acid, poly-malic acid, polysuccinates, polyfumarates, poly-hydroxybutyrates, polycaprolactones, polycarbonates, polyesteramides, poly-anhydrides, poly (amino acids), polyorthoesters, polycyano-acrylates, polyetheresters, poly(dioxanone)s, copolymers of polyethylene glycol (PEG), polyorthoesters, biodegradable polyurethanes, polyphosphazenes.

Other biocompatible polymers are polyacrylic acid, polymethacrylic acid, acrylic acid-methacrylic acid copolymers, dextran stearate, ethylcellulose, acetyl-cellulose, nitrocellulose, etc. These polymers may be homopolymers or copolymers of two or more monomers, or mixtures of the polymers.

The biologically active substance and the polymer can also be incorporated in separate organic phases. The polymer is dissolved in another above-mentioned organic non-water miscible solvent. Preferred solvents include ethyl acetate or dichloromethane. More preferred is when the solvent used to dissolve the polymer is the same solvent as that use for incorporating the biologically active substance. The thus obtained separated organic phases are poured together to form a homogenous organic phase before addition to the aqueous phase.

If the biologically active substance and/or the biodegradable polymer is not or is only slightly soluble in one of the above-mentioned solvent, for instance in the preferred solvent ethyl acetate, a sufficient amount of co-solvents such those comprised among the family of benzyl alcohol, DMSO, DMF, ethyl alcohol, methyl alcohol, acetonitrile and the like, may optionally be used in that purpose.

A better encapsulating efficiency can be achieved by an appropriate setting of the physic chemical parameters such as surfactant capacity, viscosity, temperature, ionic strength, pH and buffering potential during the homogenisation of the organic inner phase into the aqueous phase. By carefully adjusting the production parameters, the precipitating polymer can be surprisingly well formed into homogeneously dispersed particles.

Preferably, the amount of solvent used to dissolve the biodegradable polymer is kept to a minimum in order to be soluble as quickly as possible (most preferably at once) in the aqueous phase. If the amount of solvent is high, the amount of aqueous phase has to be too large on a practical point of view.

The concentration of polymer in the organic phase is adjusted to 5–90% (by weight), preferably between about 10 and 50%, depending on the polymer and solvent used.

In the case that the concentration of polymer in the organic solvent is high, the viscosity of this phase, depending on the polymer used, may be increased.

The viscosity of the polymer solution may be comprised between 1000 and 40,000 centipoise (cp) (Brookfield viscosity), more preferably between 2,000 and 30,000 cp, even more preferable between 3,000 and 20,000 cp.

Using solvents like ethyl acetate for dissolving the polymer, the solubility of the solvent in the aqueous phase is increased by lowering the temperature of both, the organic and the aqueous phases, accelerating the solvent migration and therefore also the encapsulation rate.

In process of the present invention, the temperature of the organic phase ranges between about −10° C. and 30° C., and preferably between about 0° C. and 10° C. For ethyl acetate, the temperature ranges preferably between about 2° C. and 5° C. The temperature of the polymeric organic phase and the temperature of the aqueous phase are the same or different and are adjusted in order to increase the solubility of the solvent in the aqueous phase.

The obtained organic phase for use as the inner polymer and biologically active substance containing phase is added to a aqueous outer phase under a homogenisation procedure to give microparticles.

For the homogenisation procedure, a method of creating dispersion is used. This dispersion can be realised for example with any apparatus capable of shaking, mixing, stirring, homogenising or ultrasonicating.

Different agents influencing the physico-chemical characteristics of the resultant medium may be added. For instance, surfactants, such as for example an anionic surfactant (e.g. sodium oleate, sodium stearate, sodium lauryl sulfate), a nonionic surfactant (e.g. polyoxyethylene-sorbitant fatty acid ester (Tween 80, Tween 60, products available from Atlas Powder Co, U.S.A.), a polyoxyethylene castor oil derivative (HCO-60, HCO-50, products available from Nikko Chemicals, Japan)), polyvinyl pyrrolidone, polyvinyl alcohol, carboxymethyl-cellulose, lecithin or gelatine.

In specific embodiments of the present invention, a surfactant comprised among the family of anionic, non-ionic agents or other agents capable of reducing the surface tension of the polymeric dispersion can be added. Suitably, therefore, are nonionic surfactants such as Tween (for example Tween 80), anionic surfactants, nonionic surfactant like polyvinyl alcohol or others. These surfactants can, in general, be used alone or in combination with other suitable surfactants. The concentration of the surfactant is selected in order to disperse and stabilise the polymer particles, and possibly also to give a viscosity approaching the viscosity of the organic phase.

The preferred concentration of the surfactant in the aqueous phase ranges therefore between about 0.01–50% (by weight), preferably between about 5 and 30%. The viscosity depending on the surfactant used and on its concentration ranges between about 1,000–8,000 cp (Brookfield viscosity), preferably about 3,000–5,000 cp.

Optionally salts comprised among the family of sodium chloride, potassium chloride, carbonates, phosphates and the like can be added to the aqueous phase to adjust ionic strength and to create a Zeta potential between the polymer particles, leading to particle repulsion.

Additional buffering agents may be added to the aqueous phase to maintain a specific pH. So, the internal aqueous phase may be supplemented with a pH regulator for retaining stability or solubility of the biologically active substance, such as carbonic acid, acetic acid, oxalic acid, citric acid, phosphoric acid, hydrochloric acid, sodium hydroxide, is arginine, lysine or a salt thereof. The pH of the formulations of this invention is generally about 5 to 8, preferably about 6.5 to 7.5.

The temperature of the aqueous phase can be adjusted to the temperature of the inner organic phase. The temperature range is from about −10° C. to 30° C., more preferably between 0° and 10° C. and even more preferably from between 2° C. and 5° C.

The microparticles of the present invention can be prepared in any desired size, ranging from 1 μm to about 500 μm, by varying the parameters such as polymer type and concentration in the organic phase, volumes and temperature of the organic and aqueous phase, surfactant type and concentration, homogenisation time and speed. The mean particle size of the microparticles ranges generally from 10 to 200 μm, more preferably from 20 to 200 μm, even more preferably from 30 to 150 μm.

A number of water soluble active substances can be encapsulated by the process of the present invention.

Preferably, the encapsulated soluble substance is a peptide, a polypeptide, a protein and their related pharmaceutically acceptable salts. The salt of peptide is preferably a pharmacologically acceptable salt. Such salts include salts formed with inorganic acids (e.g. hydrochloric acid, sulphuric acid, nitric acid), organic acids (e.g. carbonic acid, bicarbonic acid, succinic acid, acetic acid, propionic acid, trifluoroacetic acid) etc. More preferably, the salt of peptide is a salt formed with an organic acid (e.g. carbonic acid, bicarbonic acid, succinic acid, acetic acid, propionic acid, trifluoroacetic acid) with greater preference given to a salt formed with acetic acid. These salts may be mono-through tri-salts.

Examples of water soluble active substances which can be encapsulated in the present invention include, but are not limited to, peptides, polypeptides and proteins such as luteinizing hormone releasing hormone (LHRH) or derivatives of LHRH comprising agonists or antagonists, melanocyte stimulating hormone (MSH), thyrotropin releasing hormone (TRH), thyroid stimulating hormone (TRH), follicule stimulating hormone (FSH), human chorionic gonadotropin (HCG), parathyroid hormone (PTH), human placental lactogen, insulin, somatostatin and derivatives, gastrin, prolactin, adreno-corticotropic hormone (ACTH), growth hormones (GH), growth hormone releasing hormone (GHRH), growth hormone releasing peptide (GHRP), calcitonin, oxytocin, angiotensin, vasopressin, enkephalins, endorphin, enkephalin, kyotorphine, interferons, interleukins, tumor necrosis factor (TNF), erythropoetin (EPO), colony stimulating factors (G-CSF, GM-CSF, M-CSF), thrombopoietin (TPO), platelet derived growth factor, fibroblast growth factors (FGF), nerve growth factors (NGF), insulin like growth factors (IGF), amylin peptides, leptin, RGD peptides, bone morphogenic protein (BMP), substance P, serotonin, GABA, tissue plasminogen activator (TPA), superoxide dismutase (SOD), urokinase, kallikrein, glucagon, human serum albumin, bovine serum albumin, gamma globulin, immunomodulators (EGF, LPS), blood coagulating factor, lysozyme chloride, polymyxin B, colistin, gramicidin, bacitracin and the like.

A number of other unlimiting example of water soluble substances or particularly a water soluble form of the following substances can be encapsulated by the process of the present invention.

These substances comprise for instance anticancer drugs such as actinomycin D, bleomycin, busulfan, carboplatin, carmustine, chlorambucil, cisplatin, cladribine, cyclophosphamide, cytarabine, dacarbazine, daunorubicin, doxorubicin, estramustine, etoposide, floxuridine, fludarabine, fluorouracil, hexamethylmelamine, hydroxyurea, idarubicin, ifosfamide, asparaginase, lomustine, mechlorethamine, melphalan, mercaptopurine, methotrexate, mithramycin, mitomycin C, mitotane, mitozantrone, oxaliplatine, pentostatin, procarbazine, streptozocin, teniposide, thioguanine, thiopeta, vinblastine, vincristine and the like; antibiotics such as tetracyclines, penicillins, sulfisoxazole, ampicillin, cephalosporins, erytromycin, clindamycin, isoniazid, amikacin, chloramphenicol, streptomycin, vancomycin and the like.

Other examples of such substances comprise antivirals such as acyclovir, amantadine, and the like; antipyretics, analgesics and antiinflammatory agents include acetaminophen, acetylsalicylic acid, methylprodnisolone, ibuprofen diclofenac sodium, indomethacin sodium, flufenamate sodium, pethidine hydrochloride, levorphanol tartrate, morphine hydrochloride, oxymorphone and the like; anesthetics such as lidocaine, xylocaine and the like; antiulcer agents include metoclopramide, ranitidine hydrochloride, cimetidine hydrochloride, histidine hydrochloride, and the like anorexics such as dexedrine, phendimetrazine tartrate, and the like; antitussives such as noscapine hydrochloride, dihydrocodeine phosphate, ephedrine hydrochloride, terbutaline sulfate, isopreterenol hydrochloride, salbutamol sulfate, and the like; antiepileptics such as acetazolamide sodium, ethosuximide, phenytoin sodium, diazepam and the like; antidepressants such as amoxapine, isocarboxamide, pheneizine sulfate, clomipramine, noxiptilin, imipramine, and the like anticoagulants such as heparin or warfarin, and the like.

Other unlimiting examples comprise sedatives such as chlorpromazine hydrochloride, scopolamine methylbromide, antihistaminics such as diphenhydramine hydrochloride, ketotifen fumarate, chlorpheniramine maleate, methoxy-phenamine hydrochloride and the like.

Other unlimiting examples comprise cardiotonics such as etilefrine hydrochloride, aminophylline and the like; antiasthmatics such as terbutaline sulfate, theophylline, ephedrine, and the like; antifungals such as amphotericin B, nystatin, ketoconazole, and the like; antiarrhytmic agents such as propranolol hydrochloride, alprenolol hydrochloride, bufetolol hydrochloride, oxyprenolol hydrochloride and the like; antitubercular agents such as isoniazid, ethambutol, and the like; hypotensive, diuretic agents such as captopril, ecarazine, mecamylamine hydrochloride, clonidine hydrochloride, bunitrolol hydrochloride and the like; hormones such as prednisolone sodium sulfate, betamethasone sodium phosphate, hexestrol phosphate, dexamethasone sodium sulfate and the like; antigens from bacteria, viruses or cancers, antidiabetics such as glipizide, phenformin hydrochloride, buformin hydrochloride, glymidine sodium, methformin, and the like; cardiovascular agents such as propanolol hydrochloride, nitroglycerin, hydralazine hydrochloride, prazosin hydrochloride and the like; diuretics such as spironolactone, furosemide and the like; and enzymes, nucleic acids, plant extracts, antimalarials, psychotherapeutics, hemostatic agents, etc.

The examples that follow are set forth as an aid in understanding the present invention, and provide some examples of the many embodiments that are potentially available for the present invention. They are not intended to limit the scope of the invention.

EXAMPLE 1

62.5 mg of D-Trp$^6$-LHRH acetate (Triptorelin acetate) was added to 20 g of ethyl acetate. The peptide particles were reduced in size with a small size dispersing apparatus. This peptide suspension was added to 2 g of poly(D-L-lactide-co-glycolide) (PLGA) with a ratio of lactide to glycolide of 50:50 and a weight average molecular weight of 45,000. The mixture was stirred at room temperature until the polymer was dissolved and then placed still at 4° C. The Brookfield viscosity of this solution was 15'500 cp. (15.5 Pas).

This organic phase was poured into 675 g of aqueous phase containing 20% (w/w) of Tween 80 and 7 g of sodium chloride and having a temperature of 4° C. The homogenisation was performed with a Polytron homogeniser during 3 minutes.

The microparticles were collected right after the end of the homogenisation step by filtration. The microparticles were then vacuum dried at room temperature.

The entrapment efficiency was 93%, the mean particle size was 52 $\mu$m, and the residual ethyl acetate was 183 ppm (as determined by GC-MS).

EXAMPLE 2

1250 mg of D-Trp$^6$-LHRH acetate (Triptorelin acetate) was added to 200 g of ethyl acetate. The peptide particles were reduced in size with a small size dispersing apparatus.

40 g of poly(D-L-lactide-co-glycolide) (PLGA) with a ratio of lactide to glycolide of 50:50 and a weight average molecular weight of 45,000 were dissolved in 200 g of ethyl acetate at room temperature.

Both organic phases were poured together and stirred briefly on a magnetic stirrer. The suspension was then let to stand at 4° C. until use. This organic phase was poured into 7 kg of aqueous phase containing 20% (WAN) of Tween 80 in 67 mM phosphate buffer pH 7.4 and 70 g of sodium chloride and having a temperature of 4° C. The homogenisation was performed during 5 minutes.

The microparticles were collected right after the end of the homogenisation step by filtration. The microparticles were then vacuum dried at room temperature.

The entrapment efficiency was 76% and the mean particle size was 150 $\mu$m.

EXAMPLE 3

125 mg of bovine serum albumin was added to 20 g of ethyl acetate. The solid protein particles were reduced in size with a small size dispersing apparatus This protein suspension was added to 2 g of poly(D-L-lactide-co-glycolide) (PLGA) with a ratio of lactide to glycolide of 50:50 and a weight average molecular weight of 45,000. 20 g of additional ethyl acetate were added. The mixture was stirred at room temperature until the polymer was dissolved and then placed still at 4° C.

This organic phase was poured into 675 g of aqueous phase containing 20% (W/W) of Tween 80 in 67 mM phosphate buffer pH 7.4 and 7 g of sodium chloride and having a temperature of 7° C. The homogenisation was performed with a Polytron during 3 minutes.

The microparticles were collected right after the end of the homogenisation step by filtration.

The microparticles were then vacuum dried at room temperature. The entrapment efficiency was 76% and the mean particle size was 74 μm.

EXAMPLE 4

125 mg of D-Trp$^6$-LHRH acetate (Triptorelin acetate) was added to 5 g of ethyl acetate. The peptide particles were reduced in size with a small size dispersing apparatus.

4 g of poly(D-L-lactide) polymer were added to this peptide suspension. The mixture was stirred at room temperature until the polymer was dissolved and then placed still at 8° C.

This organic phase was poured into 675 g of aqueous phase containing 20% (W/W) of Tween 80 in 67 mM phosphate buffer pH 7.4 and 7 g of sodium chloride and having a temperature of 5° C. The homogenisation was performed with a homogeniser during 3 minutes.

The microparticles were collected right after the end of the homogenisation step by filtration. The microparticles were then vacuum dried at room temperature The entrapment efficiency was 57% and the mean particle size was 30 μm.

EXAMPLE 5

125 mg of D-Trp$^6$-LHRH acetate (Triptorelin acetate) was dissolved in 1.5 g of water.

4 g of poly(D-L-lactide-co-glycolide) (PLGA) with a ratio of lactide to glycolide of 50:50 and a weight average molecular weight of 45,000 were dissolved in 40 g of ethyl acetate at room temperature. This organic phase was cooled to 4° C.

The aqueous phase was homogenised into the organic phase. This W/O preparation was poured into 680 g of aqueous phase containing 20% (w/w) of polyoxyethylene sorbitan fatty acid ester (Tween 80) and 7 g of sodium chloride and having a temperature of 4° C. The homogenisation was performed and the microparticles were collected by filtration. The microparticles were then vacuum dried at room temperature.

The entrapment efficiency was 80% and the mean particle size was 60 μm.

EXAMPLE 6

125 mg of vapreotide acetate was dissolved in 2 g of water. 4 g of poly(D-L-lactide-co-glycolide) (PLGA) with a ratio of lactide to glycolide of 50:50 and a weight average molecular weight of 45,000 were dissolved in 40 g of ethyl acetate at room temperature. This organic phase was cooled to 4° C.

The aqueous phase was homogenised into the organic phase. This W/O preparation was poured into 800 g of aqueous phase containing 20% (w/w) of polyoxyethylene sorbitan fatty acid ester (Tween 80) and 8 g of sodium chloride and having a temperature of 4° C. The homogenisation was performed and the microparticles were collected by filtration. The microparticles were then vacuum dried at room temperature.

The entrapment efficiency was 76% and the mean particle size was 55 μm.

What is claimed is:

1. A process for the preparation of microparticles comprising at least one water-soluble substance in at least one biodegradable polymer, wherein (a) said water-soluble substance and said biodegradable polymer are first incorporated in an organic liquid phase comprising at least one organic non-water miscible solvent comprising ethyl acetate, (b) said organic phase is poured into an aqueous liquid phase having a volume which is sufficient to dissolve said organic solvent, said aqueous phase containing a surfactant, and (c) the resulting organic-aqueous phase is homogenised under conditions such that microparticle formation and their hardening, by organic solvent removal by extraction thereof into the aqueous liquid phase, are performed in one single step, without organic solvent evaporation.

2. The process of claim 1 wherein the aqueous phase contains an amount of an electrolyte.

3. The process of claim 2 wherein the electrolyte comprises sodium chloride.

4. The process according to claim 1 wherein the volumic ratio organic solvent/aqueous phase is comprised between 0.007 and 0.06.

5. The process according to claim 1 wherein the temperature of the organic phase is comprised between 2° C. and 5° C.

6. The process according to claim 1 wherein the water-soluble substance comprises a peptide, a polypeptide, a protein or the related pharmaceutically acceptable salts thereof.

7. The process according to claim 6 wherein the peptide comprises a luteinizing hormone releasing hormone (LHRH) or a derivative thereof.

8. The process according to claim 1 wherein the surfactant comprises Tween 80.

9. Microparticles obtained according to the process of claim 1.

* * * * *